United States Patent [19]

Hofmann et al.

[11] Patent Number: 4,898,170

[45] Date of Patent: Feb. 6, 1990

[54] SURGICAL KNIFE

[75] Inventors: Robert F. Hofmann, Littleton; David B. Waldock, Brentwood, England

[73] Assignees: Duckworth & Kent Surgical Instruments Limited, Hertfordshire, United Kingdom; Medical Titanium Corporation, Clearwater, Fla.

[21] Appl. No.: 206,936

[22] Filed: Jun. 10, 1988

Related U.S. Application Data

[63] Continuation of Ser. No. 891,721, Jul. 29, 1986, abandoned.

[30] Foreign Application Priority Data

Aug. 1, 1985 [GB] United Kingdom ............... 8519364

[51] Int. Cl.$^4$ .............................................. A61F 17/32
[52] U.S. Cl. .................................................. 606/166
[58] Field of Search ..................... 128/305, 303.3, 307, 128/311, 314, 315, 329 R, 329 A, 330; 604/117, 199

[56] References Cited

U.S. PATENT DOCUMENTS

| | | | |
|---|---|---|---|
| 4,006,746 | 2/1977 | Edwards | 128/305 |
| 4,071,029 | 1/1978 | Richmond et al. | 128/305 |
| 4,227,527 | 10/1980 | DeFrank et al. | 604/199 |
| 4,414,974 | 11/1983 | Dotson et al. | 128/305 |
| 4,473,076 | 9/1984 | Williams et al. | 128/305 |
| 4,499,898 | 2/1985 | Knepshield et al. | 128/305 |
| 4,516,575 | 5/1985 | Gerhard et al. | 128/305 |
| 4,534,348 | 8/1985 | Fedorov et al. | 128/305 |
| 4,552,146 | 11/1985 | Jensen et al. | 128/305 |
| 4,630,378 | 12/1986 | Kulp et al. | 128/305 |

Primary Examiner—Dalton L. Truluck
Assistant Examiner—Denise Whelton
Attorney, Agent, or Firm—Seidel, Gonda, Lavorgna & Monaco

[57] ABSTRACT

A surgical knife, especially for use by ophthalmic surgeons for performing radial keratotomy, comprises an elongate body and a head portion which receives a diamond blade and within which the blade is displaceable forwards and backwards lengthwise of the knife along a line extending at an angle of inclination to the axis of the knife body. The angle of inclination is preferably about 20°. The knife preferably incorporates a micrometer setting mechanism, adjustment of which is transmitted through the knife body to a piston located in the head portion and arranged to make contact with a knife holder for the blade. The transmission chain from micrometer to piston may include a cranked element acting on the piston.

7 Claims, 2 Drawing Sheets

SURGICAL KNIFE

This is a continuation of co-pending application Ser. No. 891,721 filed on July 29, 1986, now abandoned.

FIELD OF THE INVENTION

This invention relates to surgical knives, and is particularly concerned with surgical knives for use by ophthalmic surgeons in performing radial keratotomy.

In radial keratotomy the surgeon makes incisions which require to-and-fro and other forms of lateral motion, rather than ones made by pushing or pulling the blade. It is therefore important that a knife adapted for use in radial keratotomy should facilitate lateral to-and-fro movement of the blade.

There is also a continuing need for a surgical knife which is improved in respect of enabling the surgeon to have improved visibility of the object which is being incised. It is also important in the design of such surgical knives that the knife should be comfortable to handle, in order to facilitate precise control of the knife in use.

SUMMARY OF THE INVENTION

It is an object of the present invention to provide a surgical knife which is designed to meet these requirements.

In accordance with the present invention there is provided a surgical knife comprising an elongate body and a head portion which is adapted to receive a cutting blade and within which the blade is displaceable forwards and backwards lengthwise of the knife along a line extending at an angle of inclination to the longitudinal axis of the knife body.

One of the advantages of so constructing the knife is that the visibility afforded to the surgeon in the area in which he is working is greatly increased. The angularly inclined setting of the blade in the head portion also facilitates the lateral to-and-fro motion of the blade which is necessary when making incisions for radial keratotomy. Additionally, the "angled" nature of the knife makes it comfortable and easy to handle.

In a preferred embodiment of the surgical knife, the blade is set at and movable at an angle of about 20° to the longitudinal axis of the knife body. Although the present invention does not exclude knives with blades set at some different angle, the angle of about 20° has been found to be particularly advantageous.

Preferably, the knife incorporates a spring-loaded piston in the head portion, which bears against a blade holder. Movement of the piston towards and away from the blade holder is preferably controlled by a cranked member having one arm portion bearing against the piston and another arm portion extending axially of the knife body and movable under the control of micrometer gauge means at the rearward end of the knife.

BRIEF DESCRIPTION OF THE DRAWINGS

In order that the invention may be fully understood, one presently preferred embodiment of surgical knife in accordance with the invention will now be described by way of example and with reference to the accompanying drawings, in which.

DESCRIPTION OF THE PREFERRED EMBODIMENT

Figure 1:
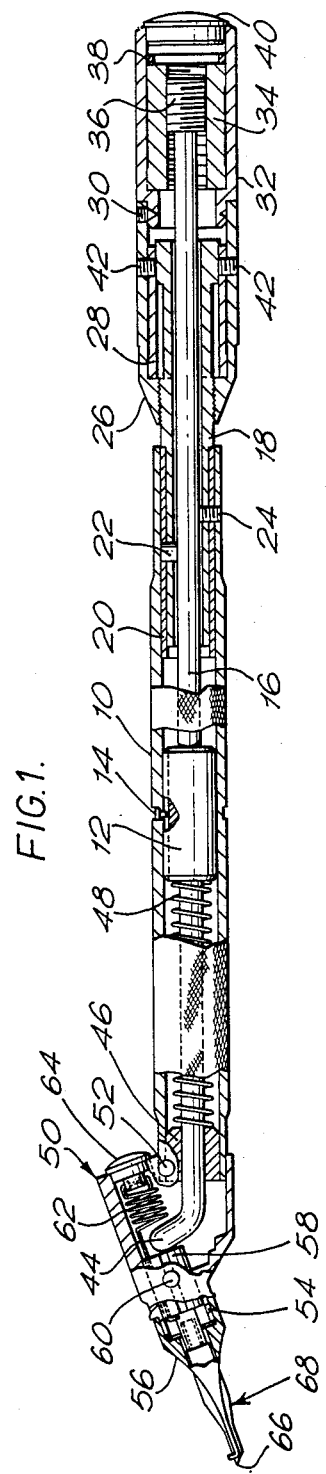
FIG. 1 is a general assembly view of the knife, partly in section.

Referring to the drawings, the surgical knife which is shown therein and which is particularly suitable for radial keratotomy is made substantially entirely of titanium or titanium alloy. The knife comprises a generally cylindrical body assembly 10 which is of reduced external diameter at its forward and rearward ends. The surface of the body assembly 10 has a fine diamond pattern knurl. The knurl is skimmed from the two reduced diameter end portions. Within the body assembly 10 there is located a guide bush 12 which has an axial groove in its outer surface, engageable by a pin 14, so that the bush is movable axially but is prevented from rotation. The rearward end of the guide bush 12 carries a centre rod 16 which extends axially rearwardly of the body assembly. A barrel 18 is fitted into the open rearward end of the body assembly 10 and is sheathed by a bush 20. A locating pin 22 is provided between the bush 20 and the barrel 18, and a locking pin 24 locates these two components in relation to the body assembly itself.

The barrel 18 is provided at its rearward end with a threaded portion to which is connected a micrometer mechanism, the purpose of which is to effect axial displacement of the centre rod within the knife. The micrometer mechanism comprises a thimble 26 which houses a plug 28. Rearwardly of the thimble 26, and connected thereto by a locking screw 30, is a second thimble 32 which houses a plug 34. Within the plug 34 is a threaded bush 36 which receives the rearward end of the centre rod 16. Rearwardly of the plug 34 is a washer 38 and a cap 40 for the thimble 32. Bush locking pins 42 are shown at each side of the thimble 26.

Fitted into the forward end of the guide bush 12 within the body assembly is a centre rod offset 44. This has a cranked member which has a relatively long linear portion extending forwardly from the guide bush 12 and a relatively short arm turned through about 60° and terminating in a rounded end portion. A centre rod steadying bush 46 is fitted within the end of the body assembly 10 with the centre rod offset 44 passing therethrough. A spring 48 has one end seated against the internal end of the centre rod steadying bush 46 and its other end seated against the forward end of the guide bush 12.

Mounted at the forward end of the main body assembly of the knife is a head portion indicated generally at 50. The head portion 50 comprises a housing which is fitted over the reduced diameter end portion of the body assembly 10 and which is secured there by a pin 52. The forward end of the housing is formed with a projecting sleeve 54 onto which a guard 56 is secured. The guard itself is shown in more detail in FIGS. 2a and 2b. Within the housing of the head portion 50 is a piston 58, shown in more detail in FIG. 3, which is displaceable forwards and backwards at an angle of about 20° to the longitudinal axis of the body, and which has its rearward end in contact with the rounded end of the centre rod offset 44. The piston 58 is provided with an axial groove in its outer surface, into which a guide pin 60 projects so that the piston is able to move axially but is prevented from rotary movement. An extension spring 62 has one end connected to the forward end of the piston 58 and has its other end connected to a head cap 64 which is fitted into the housing, the spring coils being positioned to the rear of the centre rod offset 44. This extension spring 62 thus exerts a rearward bias on the piston to maintain it in abutting contact with the end of the centre rod offset 44. A blade 66, i.e. a diamond blade, and blade holder 68 are fitted by the user into the guard 56 and into contact with the forward end of the piston 58.

The internal mechanism of the knife is designed so that small adjustments made at the rear end of the knife through the micrometer mechanism are transmitted through the centre rod 16 and centre rod offset 44 to the piston 58 and thence to the blade 66. Although various mechanisms can be employed to transmit such movements from one end of the knife to the other, the cranked arm and piston have been found to be extremely reliable and accurate in practice.

It is desirable that the shorter cranked arm portion of the centre rod offset 44 should extend at an angle of about 60° to the longitudinal axis of the knife body. This angle of inclination of 60° for the forward end portion of the centre rod offset, coupled with an offset of the piston 58 at 20° to the longitudinal central axis of the knife body has been found to provide the best results.

Figure 2A:
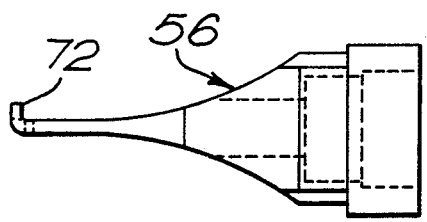
FIGS. 2a and 2b are side and plan views respectively of the guard at the leading end of the head portion of the knife.
Figure 2B:
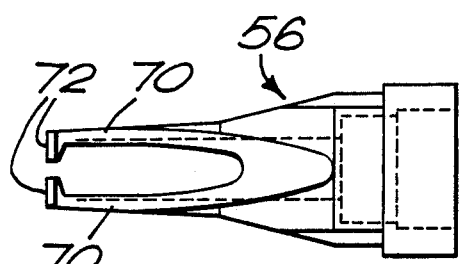
Figure 3:
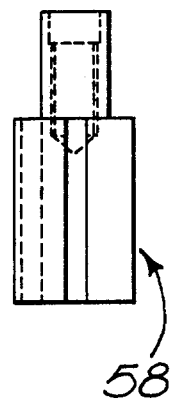
FIG. 3 is a view, on an enlarged scale, of the piston adapted to be fitted within the head portion of the knife.
Figure 4:
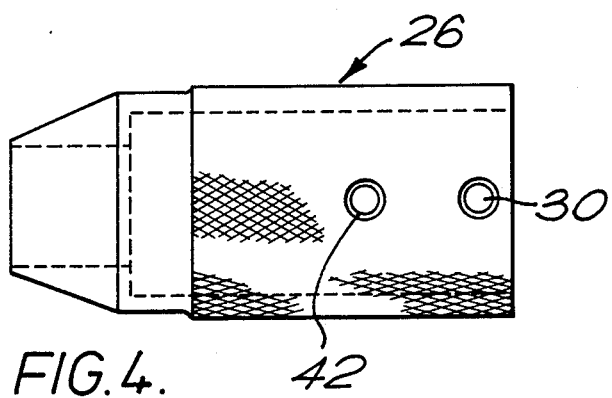
FIG. 4 is a view, on an enlarged scale, of the thimble at the rearward end of the knife; and, FIG. 5 shows a guard cap adapted to be fitted over the head portion of the knife after final assembly.

Reference to FIGS. 2a and 2b will show the details of the guard 56. As shown, the guard comprises two legs 70 which extend one on each side of the central diamond blade. These legs have upturned end portions 72 and not only guard the blade but facilitate the lateral to-and-fro movements which are necessary for radial keratotomy. These upturned end portions 72 of the guard legs 70 also provide sight lines for the surgeon when using the knife. The diamond blade 66 is preferably a double edge blade subtending an angle at the tip of 60°. It is preferably mounted transversely so that the surgeon can perform lateral to-and-fro movements, using the knife like a draftsman's scribe.

Figure 5:
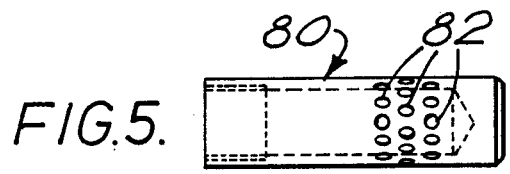

FIG. 5 shows a guard cap 80 which is designed to be fitted over the end of the head portion of the knife. This guard cap 80 is fitted over the head after final assembly of the knife and may be made for example of glass-filled PTFE. It comprises a cylindrical cap which is provided with a plurality of vent holes 82 equally spaced around its periphery. The purpose of the cap is protective, i.e. so that the diamond blade is not damaged, with the holes 82 permitting sterilization of the knife to be carried out when the blade is within the protective cap.

The protective cap may be a push fit or a screw fit on the head portion.

We claim:

1. A surgical knife comprising a cutting blade, an elongated body, a head portion for receiving said cutting blade and adjustment means permitting adjustment of said blade within said head portion forwards and backwards lengthwise of the knife along a line extending at an angle of inclination to the longitudinal axis of the knife body, the head portion comprising a displaceable piston projecting into a chamber into which a blade holder for the blade is received, spring means acting to exert a biasing force on the piston, and a cranked member extending into the head portion of the knife body and having one arm bearing against the piston and another arm extending axially of the knife body.

2. A surgical knife according to claim 1, in which the head portion is adapted to hold the blade such that the blade is set at and movable at an angle of about 20° to the longitudinal axis of the knife body.

3. A surgical knife according to claim 1, in which the axis of said one arm makes an included angle of about 60° with the forward extension of the axis of said another arm.

4. A surgical knife according to claim 1, wherein said adjustment means includes micrometer gauge means at the end of the knife body remote from the head portion, said gauge means controlling movement of said cranked member and thus displacement of said piston.

5. A surgical knife according to claim 1, wherein said adjustment means includes micrometer gauge means at the end of the knife body remote from the head portion, and direct mechanical transmission means between the gauge means and the head portion through the body of the knife, said transmission means comprising elongate rod means capable of linear displacement without rotation.

6. A surgical knife according to claim 1, which includes a guard fitted to the head portion to protect the blade which is adapted to be inserted, in a blade holder, into said guard, the guard comprising two legs extending forwardly one on each side of the blade, with each leg having an upturned portion at its forward end terminating in a flat surface extending transversely to the longitudinal axis of the head portion.

7. A surgical knife according to claim 1, which includes a protective cap to be removably fitted to the head portion over the forward end thereof, said cap being provided with a plurality of holes for the passage of a sterilizing fluid therethrough.

* * * * *